(12) United States Patent
Fecteau et al.

(10) Patent No.: US 10,973,452 B2
(45) Date of Patent: Apr. 13, 2021

(54) WEARABLE PHYSIOLOGICAL DATA ACQUIRER AND METHODS OF USING SAME

(71) Applicant: ICENTIA INC., Québec (CA)

(72) Inventors: Pierre Fecteau, St-Augustin-de-Desmaures (CA); Yannick Le Devehat, Québec (CA); Pierre Paquet, Quebec (CA)

(73) Assignee: ICENTIA INC., Québec (CA)

( * ) Notice: Subject to any disclaimer, the term of this patent is extended or adjusted under 35 U.S.C. 154(b) by 137 days.

(21) Appl. No.: 15/553,680

(22) PCT Filed: Feb. 25, 2016

(86) PCT No.: PCT/CA2016/050192
§ 371 (c)(1),
(2) Date: Aug. 25, 2017

(87) PCT Pub. No.: WO2016/134473
PCT Pub. Date: Sep. 1, 2016

(65) Prior Publication Data
US 2018/0014743 A1  Jan. 18, 2018

Related U.S. Application Data

(60) Provisional application No. 62/121,997, filed on Feb. 27, 2015.

(51) Int. Cl.
*A61B 5/259* (2021.01)
*A61B 5/00* (2006.01)
(Continued)

(52) U.S. Cl.
CPC ............ *A61B 5/259* (2021.01); *A61B 5/0006* (2013.01); *A61B 5/274* (2021.01); *A61B 5/296* (2021.01);
(Continued)

(58) Field of Classification Search
CPC . A61B 5/04087; A61B 5/0416; A61B 5/0492; A61B 5/0428; A61B 2560/0443;
(Continued)

(56) References Cited

U.S. PATENT DOCUMENTS 5,704,365 A    1/1998  Albrecht et al.
6,580,942 B1   6/2003  Willshire
(Continued)

FOREIGN PATENT DOCUMENTS

CA      2651203 A1    8/2007
JP      06197875      7/1994
(Continued)

*Primary Examiner* — Tammie K Marlen
(74) *Attorney, Agent, or Firm* — Norton Rose Fulbright Canada LLP; Alexandre Daoust

(57) ABSTRACT

One of the methods includes positioning the physiological data acquirer on the body of a mammal with the electrodes exposed to the body; activating a data acquisition mode of operation of the physiological data acquirer and acquiring physiological data from the user when in said data acquisition mode. Another one of the methods includes extracting the acquired data using a data extraction device.

23 Claims, 10 Drawing Sheets

(51) Int. Cl.
*A61B 5/30* (2021.01)
*A61B 5/274* (2021.01)
*A61B 5/296* (2021.01)

(52) U.S. Cl.
CPC ........ *A61B 5/30* (2021.01); *A61B 2560/0412* (2013.01); *A61B 2560/0443* (2013.01); *A61B 2562/227* (2013.01)

(58) Field of Classification Search
CPC . A61B 2560/0412; A61B 5/259; A61B 5/274; A61B 5/30; A61B 5/0006; A61B 2562/227

See application file for complete search history.

(56) References Cited

U.S. PATENT DOCUMENTS

| | | | |
|---|---|---|---|
| 6,605,046 B1 | 8/2003 | Del Mar | |
| 6,881,191 B2 | 4/2005 | Oakley et al. | |
| 7,206,360 B2 | 4/2007 | Tarler | |
| 7,797,039 B2 | 9/2010 | Koivumaa et al. | |
| 8,150,502 B2 | 4/2012 | Kumar et al. | |
| 8,160,682 B2 | 4/2012 | Kumar et al. | |
| 8,244,335 B2 | 8/2012 | Kumar et al. | |
| 2003/0069510 A1 | 4/2003 | Semler | |
| 2006/0030782 A1 | 2/2006 | Shennib | |
| 2006/0224072 A1 | 10/2006 | Shennib | |
| 2006/0264767 A1 | 11/2006 | Shennib | |
| 2007/0149888 A1 | 6/2007 | Kohls et al. | |
| 2007/0255184 A1 | 11/2007 | Shennib | |
| 2008/0091089 A1 | 4/2008 | Guillory et al. | |
| 2008/0195169 A1 | 8/2008 | Pinter et al. | |
| 2009/0076336 A1 | 3/2009 | Mazar et al. | |
| 2011/0092834 A1 | 4/2011 | Yazicioglu et al. | |
| 2011/0160601 A1 | 6/2011 | Wang et al. | |
| 2012/0029306 A1 | 2/2012 | Paquet et al. | |
| 2012/0029307 A1* | 2/2012 | Paquet | A61B 5/0022 600/301 |
| 2012/0029309 A1 | 2/2012 | Paquet et al. | |
| 2012/0088998 A1 | 4/2012 | Bardy et al. | |
| 2012/0110226 A1 | 5/2012 | Vlach et al. | |
| 2012/0310070 A1 | 12/2012 | Kumar et al. | |
| 2016/0007877 A1* | 1/2016 | Felix | A61B 5/04325 600/523 |

FOREIGN PATENT DOCUMENTS

| | | |
|---|---|---|
| WO | 2011143490 A2 | 11/2011 |
| WO | 2012015759 A2 | 2/2012 |
| WO | 2012015761 A2 | 2/2012 |

* cited by examiner

WEARABLE PHYSIOLOGICAL DATA ACQUIRER AND METHODS OF USING SAME

Physiological data such as respiratory rate, heart rate or electrocardiographs acquired directly at the hospital can be used by physicians to diagnose or follow up on some persistent health conditions (called chronic conditions). Since the condition is persistent, the acquisition of the physiological data over a short period of time is usually sufficient to serve the purpose. However, the diagnosis of intermittent conditions (also called paroxysmal conditions) or the necessity to follow up on certain conditions over a long period of time can pose a challenge. To this end, wearable physiological acquisition systems have been used. These devices typically had an integrated power supply (battery) and memory, allowing the patient to essentially continue his/her normal activities of daily living during the process. Devices such as described in US applications US 2012/0029306, or PCT publications WO 2012/015761 and WO 2012/015759 have been described in patent publications where they take the form of a water-resistant and flexible bandage connectable at opposite ends to two off-the-shelf electrodes (e.g. such as manufactured by 3M, etc.) via a male-female snap-button connection. Those said devices adhere directly to the body of the patient, via the electrodes, subsequently to snapping the female snap-button connection of the device to the male snap connection of the off-the-shelf electrode and removal of an adhesive-covering layer from the face of the electrodes opposite the male snap button connection. It was known to record physiological data in a built-in memory and to require the data to be transferred to an external system once the recording period is completed. The access to the internal memory was done by manually cutting the water-resistant enclosure of the device, requiring a significant amount of manual intervention which was inconvenient both for efficiency and hygiene issues.

BACKGROUND

Moreover, in ECG data acquisition devices, signal quality will be impacted by various sources of undesired signals, later referenced as noise. The most common categorization for these sources of noise are: external electrical noise, physiological noise and baseline noise originating from the electrode to skin interface. For example, long signal leads can induce external electrical noise through cable connections to the patient. Also, body movements, generating muscular activity localized in the vicinity of the ECG electrodes is the most common source of physiological noise. Muscular contractions produces electrical potentials (EMG—electromyography signals) that are additive to the ones created by the heart. Since the frequency content of EMG is comparable to the frequency content of ECG, conventional signal processing techniques will not be efficient at removing EMG noise to improve ECG signal quality.

Accordingly, there always remains room for improvement.

SUMMARY

In accordance with one aspect, there is provided a method of using a physiological data acquirer housed in a generally bandage-like housing having at least two connectors made integral to the housing and being adapted to matingly receive corresponding electrodes externally to the housing, the physiological data acquirer having an integrated battery, the method comprising: connecting the connectors of the physiological data acquirer to corresponding mating connectors of an external device; and extracting data from the physiological data acquirer to the external device via the connected connectors.

In accordance with another aspect, there is provided a method of using a physiological data acquirer being wearable on a body of a mammal with electrodes in contact with the body and having an integrated battery, the electrodes being connected to the physiological data acquirer via at least two connectors each having at least two independent electrical paths, the method comprising: positioning the physiological data acquirer on the body of the user with the electrodes exposed to the body; acquiring a first set of physiological data from the mammal with the physiological data acquirer, via the electrodes, across a first one of the electrical paths of both connectors; and simultaneously to the acquiring of the first set of physiological data, acquiring a second set of physiological data from the mammal with the physiological data acquirer, via the electrodes, across a second one of the electrical paths of both connectors.

In accordance with another aspect, there is provided a data extraction device for extracting data from a physiological data acquirer having at least two connectors made integral to the housing and being adapted to matingly receive corresponding electrodes externally to the housing, the data extraction device comprising: connectors matingly connectable to the connectors of the physiological data acquirer; and a data extractor unit for extracting data from the physiological data acquirer via the connected connectors.

In accordance with another aspect, there is provided a physiological data acquirer being wearable on a body of a user with electrodes in contact with the body and having an integrated battery, the physiological data acquirer comprising: means for positioning the physiological data acquirer on the body of the user with the electrodes exposed to the body; means for activating a data acquisition mode of operation of the physiological data acquirer upon detecting a change of the impedance between the electrodes; and means for acquiring physiological data from the user when in said data acquisition mode.

In accordance with another aspect, there is provided a physiological data acquirer being wearable on a body of a mammal with electrodes in contact with the body and having an integrated battery, the electrodes being connected to the physiological data acquirer via at least two connectors each having at least two independent electrical paths, the physiological data acquirer further comprising: a first acquiring unit for acquiring a first set of physiological data from the mammal with the physiological data acquirer, via the electrodes, across a first one of the electrical paths of both connectors; and a second acquiring unit for acquiring, simultaneously to the acquiring of the first set of physiological data, a second set of physiological data from the mammal with the physiological data acquirer, via the electrodes, across a second one of the electrical paths of both connectors.

In accordance with another aspect, there is provided a method of using a physiological data acquirer housed in a water-resistant housing having at least two connectors made integral to the housing and being adapted to connectingly receive corresponding electrodes externally to the housing, the physiological data acquirer having an integrated battery, the method comprising: connecting the female snap-button connectors of the physiological data acquirer to corresponding male connectors of an external device; and extracting data from the physiological data acquirer via the connected female snap-button and male connectors.

In accordance with another aspect, there is provided a method of using a physiological data acquirer housed in a water-resistant housing having at least two female snap-button connectors made integral to the housing, each snap button comprising at least two electrical signal connections and being adapted to snappingly receive corresponding electrodes externally to the housing, the physiological data acquirer having an integrated battery, the method comprising: positioning the physiological data acquirer on the body of the user with the electrodes exposed to the body; and acquiring physiological data from the user.

The expression physiological data is used in this application to refer to data concerning one or more of heart rate/heart rate variability, electrocardiographs (ECG), electromyography signals (EMG), respiratory rate, activity level, body position, body temperature, etc.

Many further features and combinations thereof concerning the present improvements will appear to those skilled in the art following a reading of the instant disclosure.

DESCRIPTION OF THE FIGURES

In the figures.

DETAILED DESCRIPTION

Figure 1A:
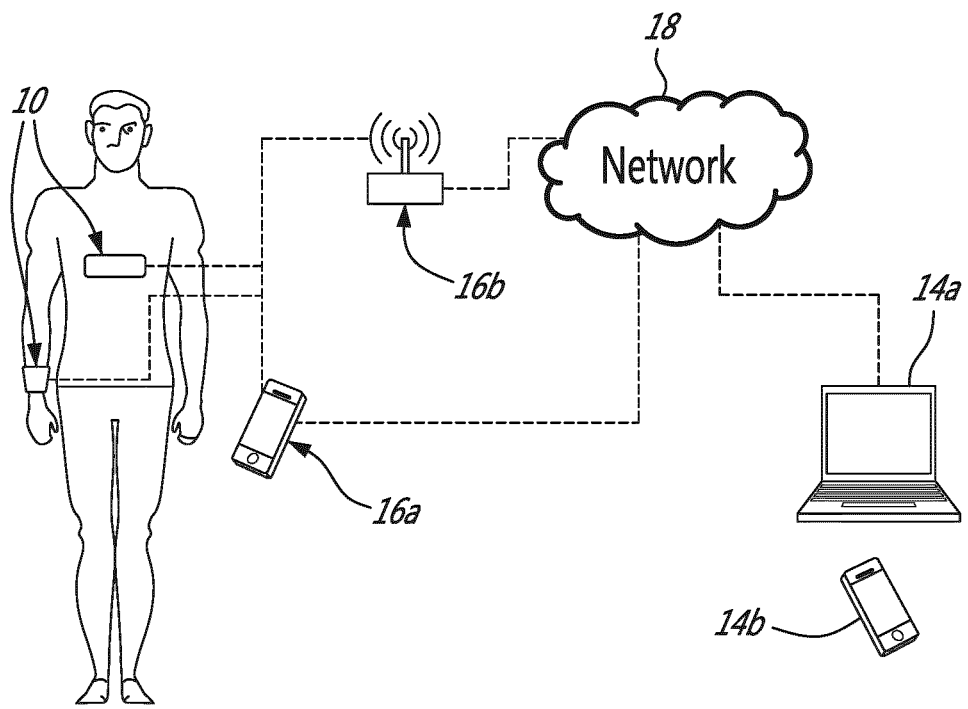
FIGS. 1A and 1B show example embodiments of physiological data acquirers.
Figure 1B:
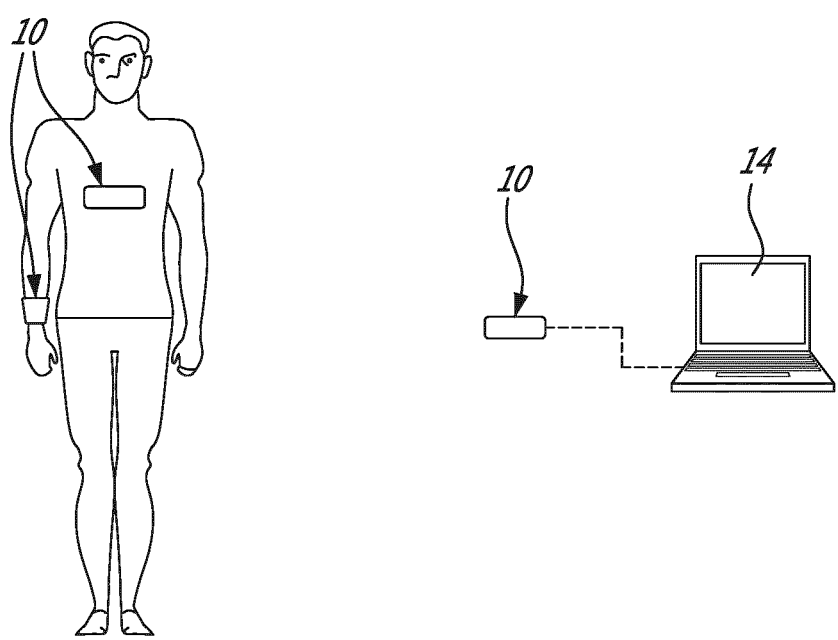

FIGS. 1A and 1B both show an example of wearable physiological data acquirer 10 wearable on a wrist of a user and an example of a wearable physiological data acquirer 10 wearable on the chest of the user. In each case, electrodes are maintained in contact with the skin of the user during use, and physiological data concerning the user can be acquired via the electrodes.

In FIG. 1A, the physiological data acquirers 10 have an integrated transmitter allowing transmittal of the acquired data to a computer such as a remote computer 14a, a tablet, a smartphone 14b, or other device suitable for an external person to evaluate or analyze the acquired data. The acquired data can be sent via a relay device such as a smartphone 16a or wireless base station 16b connected to a network 18 such as the Internet, for instance.

In FIG. 1B, the physiological data acquirers 10 have an integrated memory allowing in situ recording of the data. The user can wear the acquirer 10 for a predetermined period of time for instance, and the acquirer 10 then be removed from the person and connected to a computer 14 where data is downloaded and analyzed.

Figure 1C:
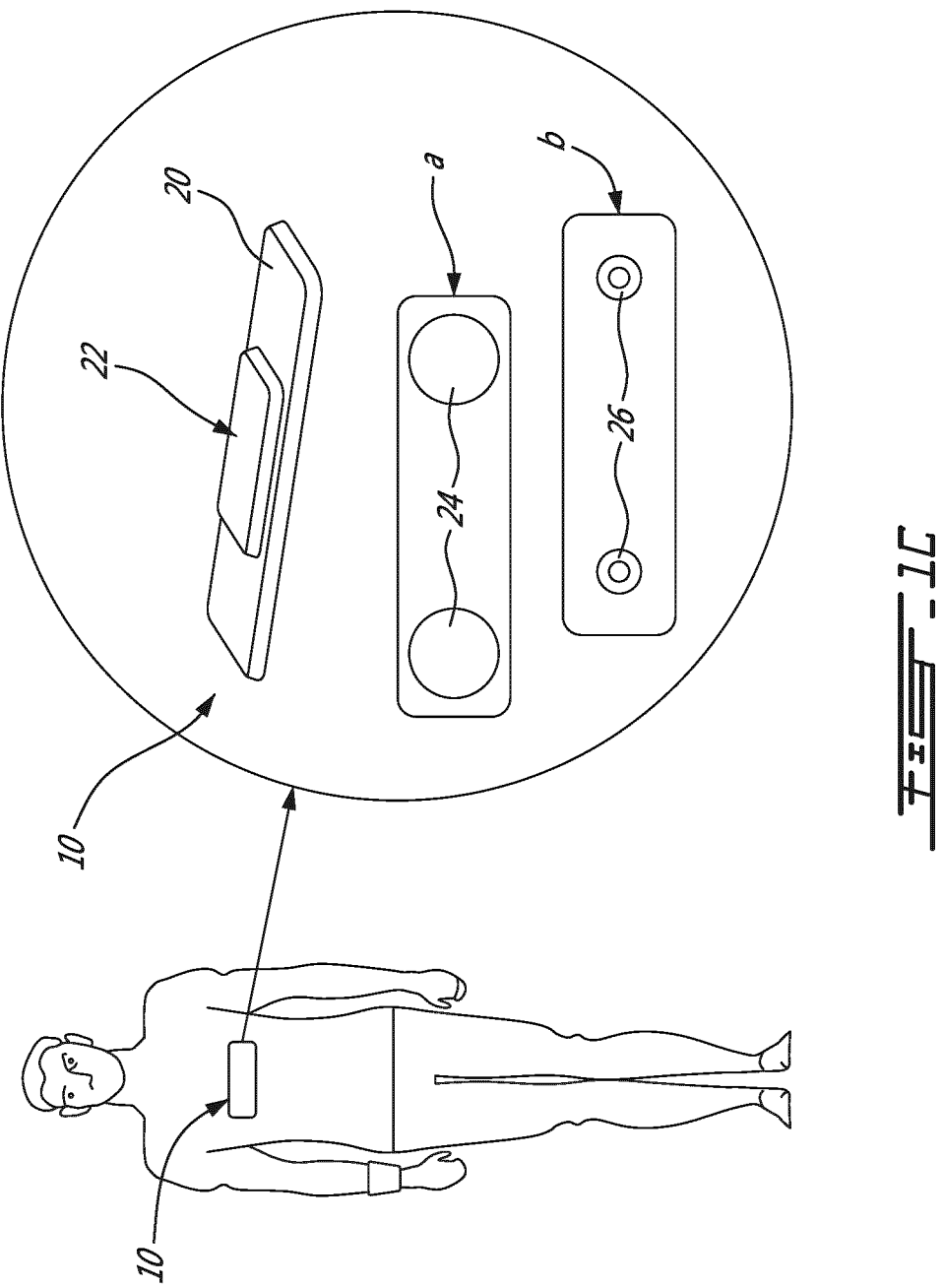
FIG. 1C shows two example embodiments of a physiological data acquirer wearable on a torso of a user.
Figure 2:
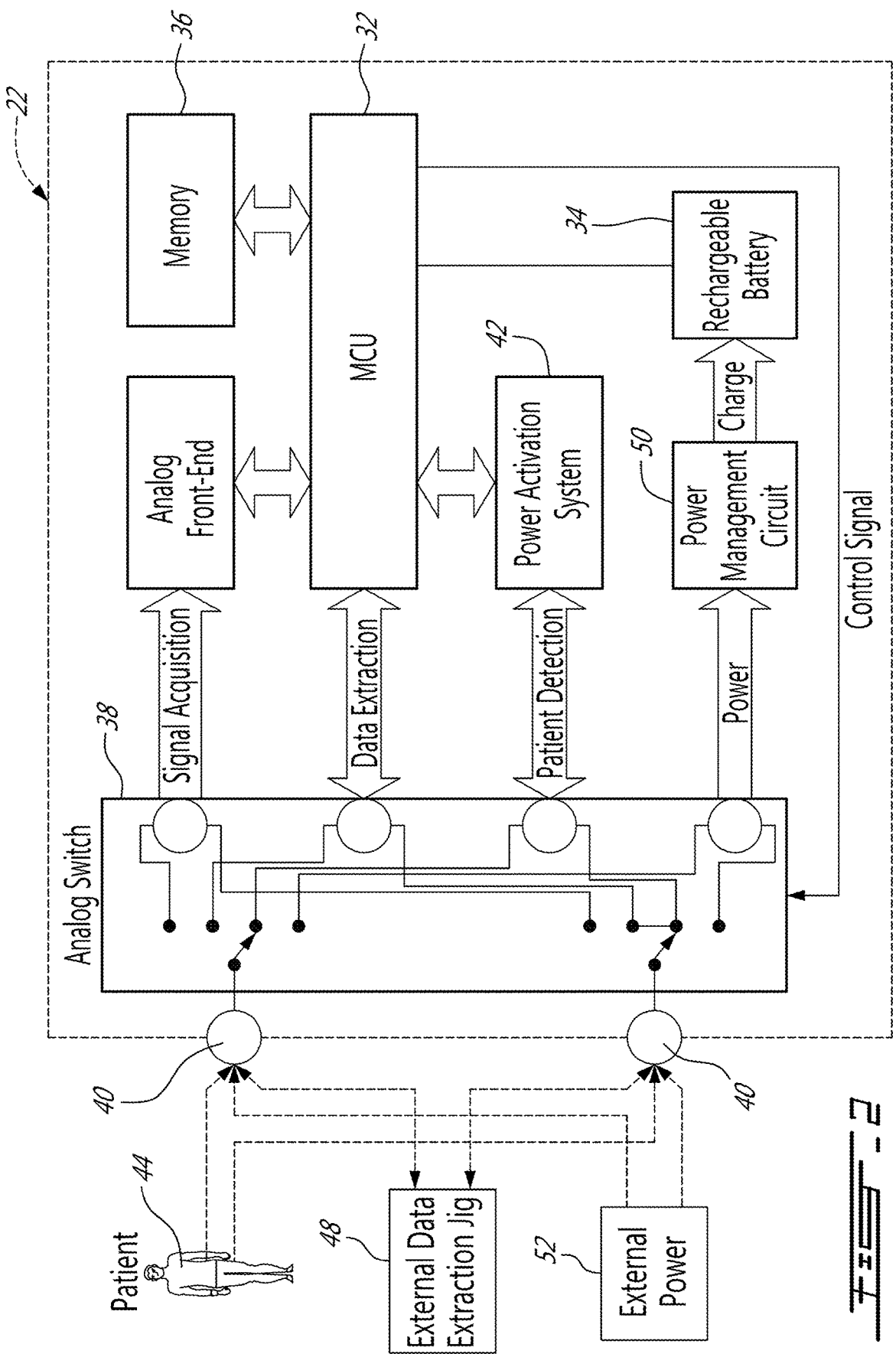
FIG. 2 is a schematic view showing operating modes of the physiological data acquirer circuit of the physiological data acquirer of FIGS. 1A and 1B.

FIG. 1C shows an example of a physiological data acquirer 10 generally having a flexible bandage-like housing 20 made of a water-resistant material forming a seal around an encapsulated electronic circuit 22 which is housed therein and used for acquiring physiological data (such as an ECG for instance) from a patient. As shown at a) and b), respectively, the physiological data acquirer 10 can have integrated electrodes 24, or be provided with snap-button connectors 26 adapted to snappingly receive off-the-shelf electrodes (sometimes referred to as electrode pads), for instance. Internally to the water-resistant housing 20, the electronics of the physiological data acquirer 10 are electrically connected to the snap-button connectors 26. The electrodes typically have a male snap-button connector on an outer face thereof, and an adhesive inner face which is covered by a protective film until the time of use. In alternate embodiments, different electrodes can be used such as gel electrodes or foam+liquid electrodes, and the electrodes can have an adhesive surface or not.

During use of the embodiment such as shown at b) of FIG. 1C, to acquire an ECG signal from a patient, the electrodes are snapped into the snap-button connectors 26 of the physiological data acquirer 10, which forms both a mechanical and an electrical connection, and the protective film are removed from the inner face of the electrodes which are then applied to the patient. The electrodes interface the physiological data signal from the patient and the signal is transmitted to the encapsulated electronic circuit 22 across the snap-button connectors 26.

Figure 3:
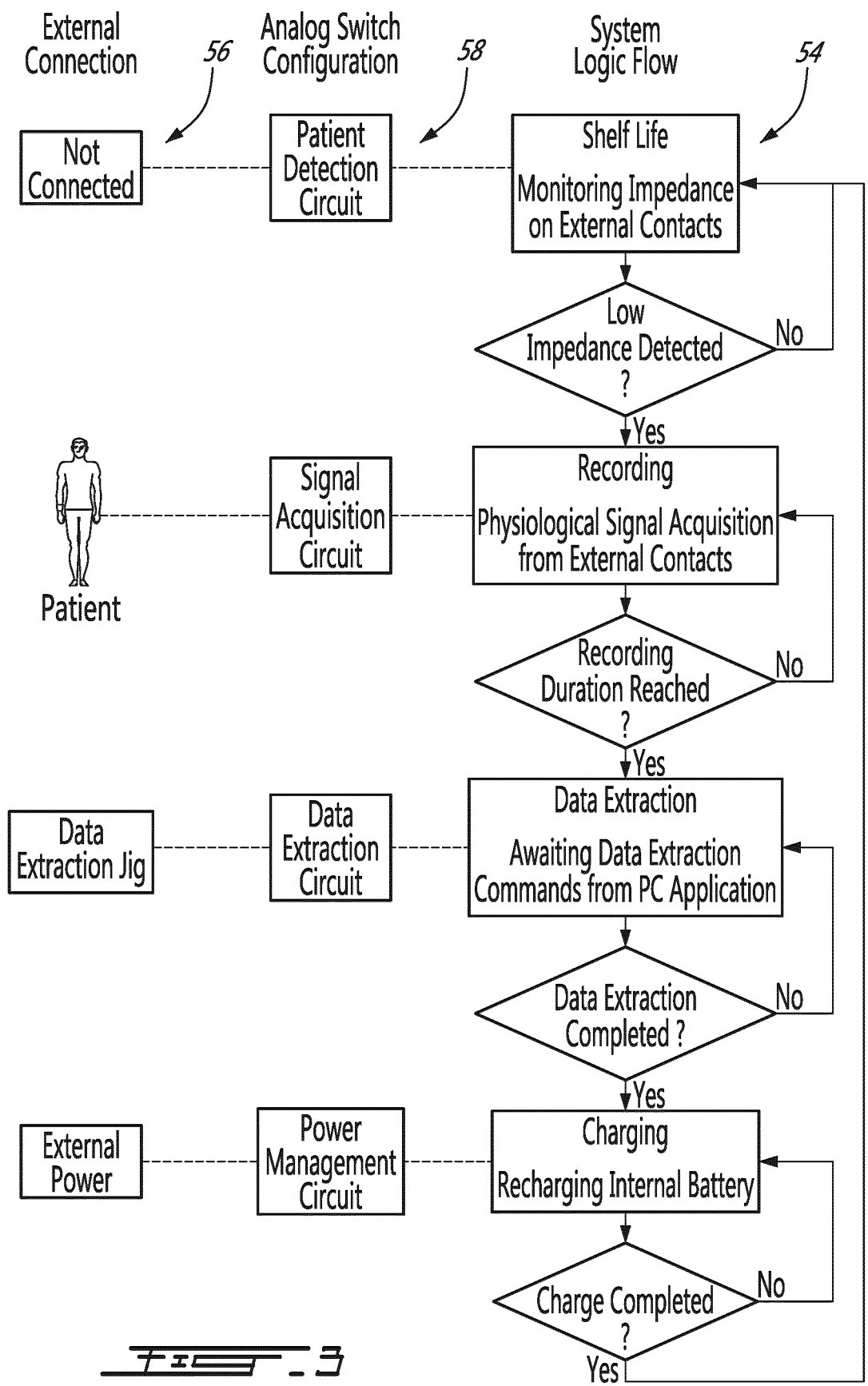
FIG. 3 is a flow chart showing the position of the analog switch and the state of an ECG signal reader.

During an acquisition mode of operation of the physiological data acquirer 10, a micro-controller unit 32 (MCU) of the physiological data acquirer 10, powered by a battery 34 also housed in the physiological data acquirer 10, stores the received signal into a memory 36 (also housed in the physiological data acquirer 10). These components can thus be said to form part of a signal acquisition module of the encapsulated electronic circuit 22 of the physiological data acquirer 10. An example of the signal acquisition module is shown in FIG. 3.

When the physiological data acquirer 10 is used in the acquisition mode, it can be said to be activated. For practical reasons, it can be preferred to provide low-cost physiological data acquirers which can have a long shelf life prior to activation. To this end, in this example, the physiological data acquirer 10 can be used in a 'sleep' mode prior to activation. During the sleep mode, only minimal functions of the physiological data acquirer 10 are maintained. This can include maintaining operation of an internal clock of the physiological data acquirer 10, for instance. For the sake of simplicity, the same expression "sleep mode" is also used to encompass complete inactivity of the physiological data acquirer 10 in this specification.

In this example, the switching from a sleep mode into the activation mode is performed automatically, which can help avoid human manipulation errors. To this end, an analog switch 38 is incorporated in the acquisition module. More specifically, when the acquisition module is in the sleep mode, the analog switch 38 operates in a 'detection' mode.

The objective of the 'detection' mode is to detect when the monitor is placed on the patient in order to trigger the automatic activation. This detection can be done upon detecting a change of impedance between the two electrical contacts 40. When the two contacts 40 are placed in contact with the patient 44, the impedance, which was could formerly be considered infinite, significantly diminishes. The acquisition module 30 can thus be activated and place the analog switch 38 into the acquisition mode. The electrodes can thence record the physiological data signal. The analog switch 38 can be said to shunt the signal to the correct module at an opportune moment. The analog switch 38 can thus direct the signal to a power activation system 42 (or power activation module) during the sleep mode, and the power activation system 42 can detect an activation signal when electrodes have been connected to the snap-button connectors 26 and/or when the electrodes have been applied to the patient 44, and activate the data acquisition mode based on this signal, at which point the analog switch 38 shunts the signal to the acquisition module.

Before use, from an electrical perspective, there is an open circuit between the electrodes of the physiological data acquirer 10, which can be considered to create a virtually infinite impedance between the electrodes. Upon connection of the ECG signal acquisition module to the patient skin, an electrical path is created and a measurable impedance appears between the contacts 40. Normally when proper skin preparation is done before connection of the electrodes to the patient skin, that impedance typically ranges from a couple of tens of kilo ohms to about a few hundreds of kilo ohms. By detecting that change in impedance, one can take action depending on the value of that impedance, which can be evaluated by, for example, measuring the current flowing between the electrical contacts 40. Such action can take different forms, such as:

Do nothing (the physiological data acquirer 10 remains in its current state).

Inform the caregiver through a user interface of the physiological data acquirer 10 that installation is not correct (for example if a change in impedance is detected, but the impedance measurement is above a certain value).

Switch the physiological data acquirer 10 from sleep mode to acquisition mode."

In this example, the amount of time elapsed since activation of the data acquisition mode can be monitored, which can be achieved via the internal clock of the acquisition module, for instance, and the power activation system 42 can also be used to automatically trigger de-activation of the data acquisition mode (i.e. switching from the activation mode back into the sleep mode) once a predetermined amount of time has elapsed. The predetermined amount of time can be a few days, for instance.

Once data acquisition is complete, the acquisition module can go into another mode, which will be referred to herein as the battery saving mode herein in order to easily distinguish it from the "sleep mode", although the exact operation of the physiological data acquirer 10 can be the same or different in both modes depending on the application. During the battery saving mode, and in embodiments where an internal clock is used, the amount of time since activation continues to be calculated in order to allow a precise determination of the temporal location of any recorded event upon data extraction. Preferably, the battery 34 is selected in order for the operation of the timer to be maintained for a satisfactory period of time. The analog switch can then shunt to data extraction mode. The patient can return the physiological data acquirer 10 to a data treatment center for analysis. For efficiency and sanitary purposes, the physiological data acquirer 10 of this example has a function (or data extraction module or circuit) allowing the data to be extracted from the memory 36 using the snap-button connectors 26. This can be performed by connecting the snap-button connectors 26 to an external device such as an external data extraction jig 48 having corresponding snap-button connectors. At this point, the analog switch 38 can shunt the snap-button connectors 26 to the MCU 32 for data extraction, for instance.

In this example, the physiological data acquirer 10 also has a recharging module, or power management circuit 50, which can be used to prolong the useful life of the physiological data acquirer 10, for instance. In this embodiment, the battery 34 is rechargeable, and the physiological data acquirer 10 can be connected to an external device such as an external power source 52, via the snap-button connectors 26, to recharge the battery 34. More specifically, the analog switch 38 can shunt the electrical power to the power management circuit 50 upon operation in the battery charging mode, and the power management circuit 50 can manage the charging of the battery 34, returning the circuit to sleep mode and the analog switch 38 to detection mode upon full charge of the battery 34.

An example system flow 54 is shown in FIG. 3 where for different steps of the system flow 54, the external connection 56 and the analog switch configuration 58 are identified. Upon each state transition, the analog switch is automatically reconfigured by the system.

Figure 4:
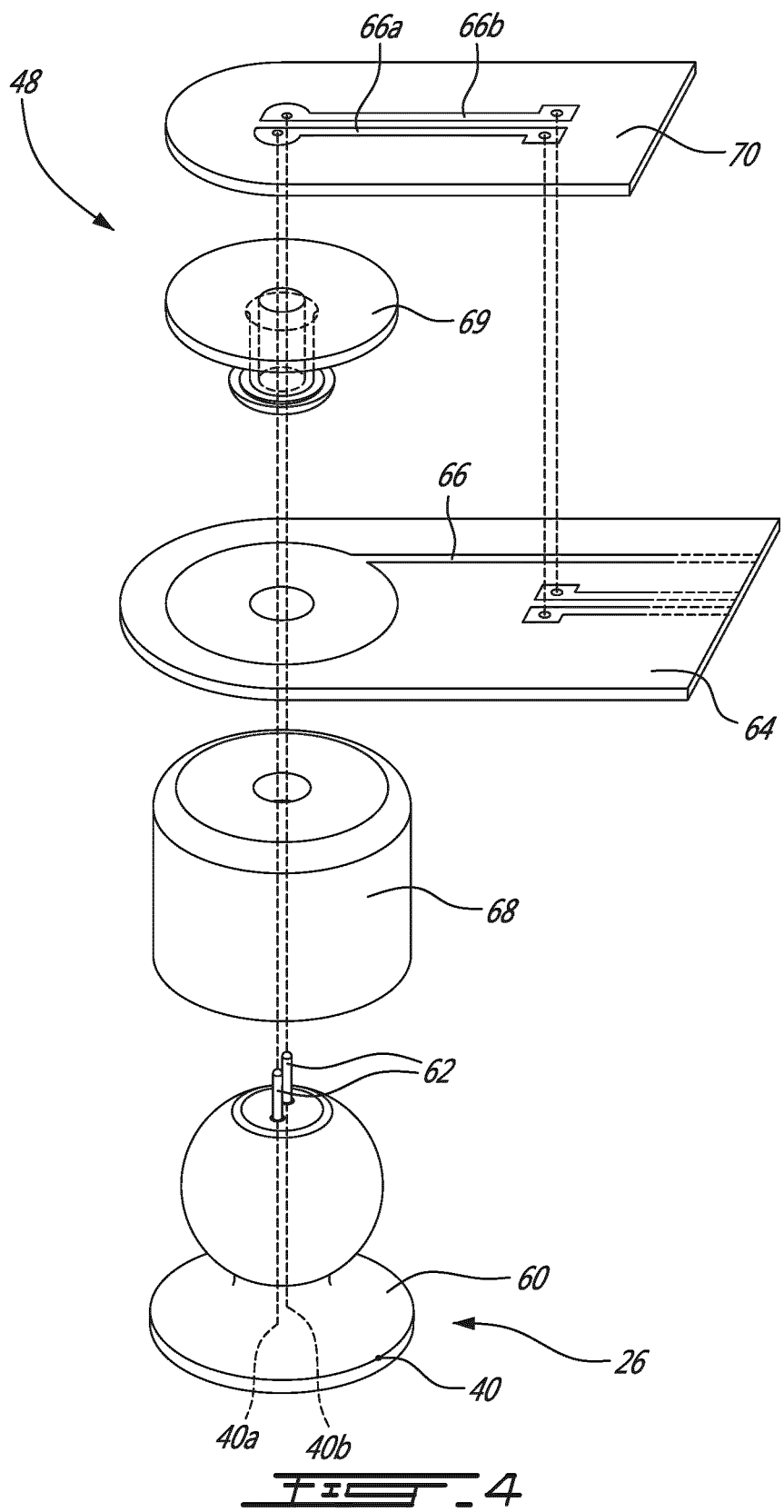
FIG. 4 is an exploded view showing an example of a snap-button connector having more than one electrical connection therein, to address data extraction speed.
Figure 5:
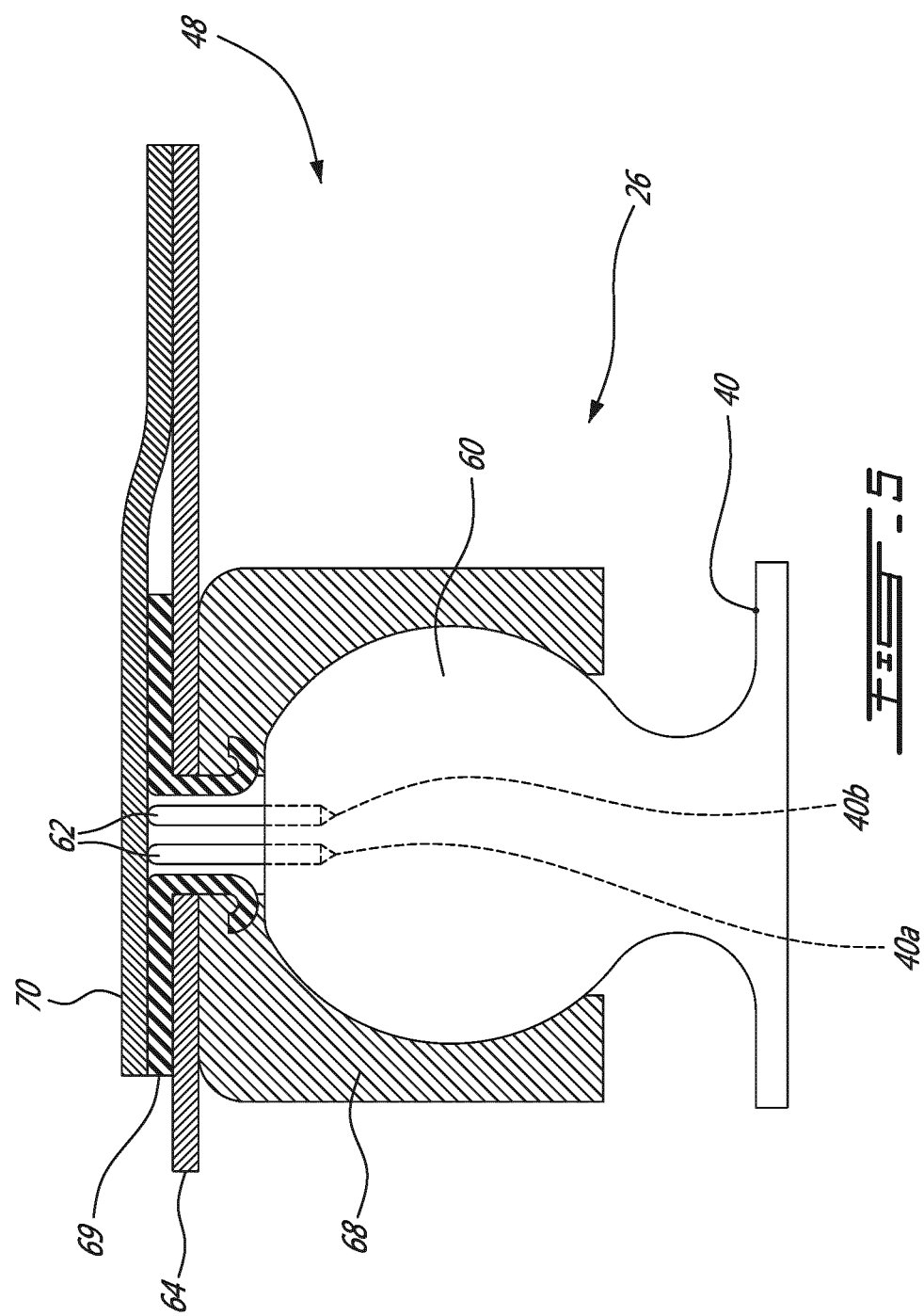
FIG. 5 is a cross-sectional view of the snap-button connector of FIG. 4.

Referring back to the data extraction mode, the data transfer speed can be limited when using only two electrical contacts 40. However, each one of the connectors can be designed to have a plurality of electrical contacts 40. For instance, FIGS. 4 and 5 show an embodiment where the connectors 26 are snap-button like and have a plurality of independent electrical paths running through its center hole. The data extraction jig 48 can be designed accordingly, in order to allow reaching a better data transfer speed. Simply providing two electrical contacts 40 at each snap-button connector 26, for instance, can allow achieving a high speed SPI data transfer.

For instance, FIG. 4 shows that the snap-button connector 26 has first, second and third electrical contacts respectively shown at 40, 40a and 40b. The electrical contacts 40, 40a and 40b are provided on a modified snap button stud 60 with spring pins 62. In this example, the data extraction jig 48 has a main PCB module 64 having a first electrical path 66 connectable to the first electrical contact 40 via a snap button socket 68. The snap button socket 68 is retained to the main PCB module 64 by a snap button post 69. The main PCB module 64, the snap button socket 68 and the snap button post 69 each have a concentric center hole allowing the spring pins 62 to pass therein and to protrude on another side of the main PCB module 64 when the snap-button connector 26 is snappingly engaged with the data extraction jig 48. In this embodiment, a complementary PCB module 70 is provided on the other side of the main PCB module 64 to electrically engage with the protruding spring pins 62 of the modified snap button stud 60. The complementary PCB module 70 has second and third electrical paths 66a and 66b which can each connect to a respective one of the spring pins 62. The second and third electrical paths 66a and 66b can then connect with corresponding electrical paths of the main PCB module 64 during use.

Figure 6:
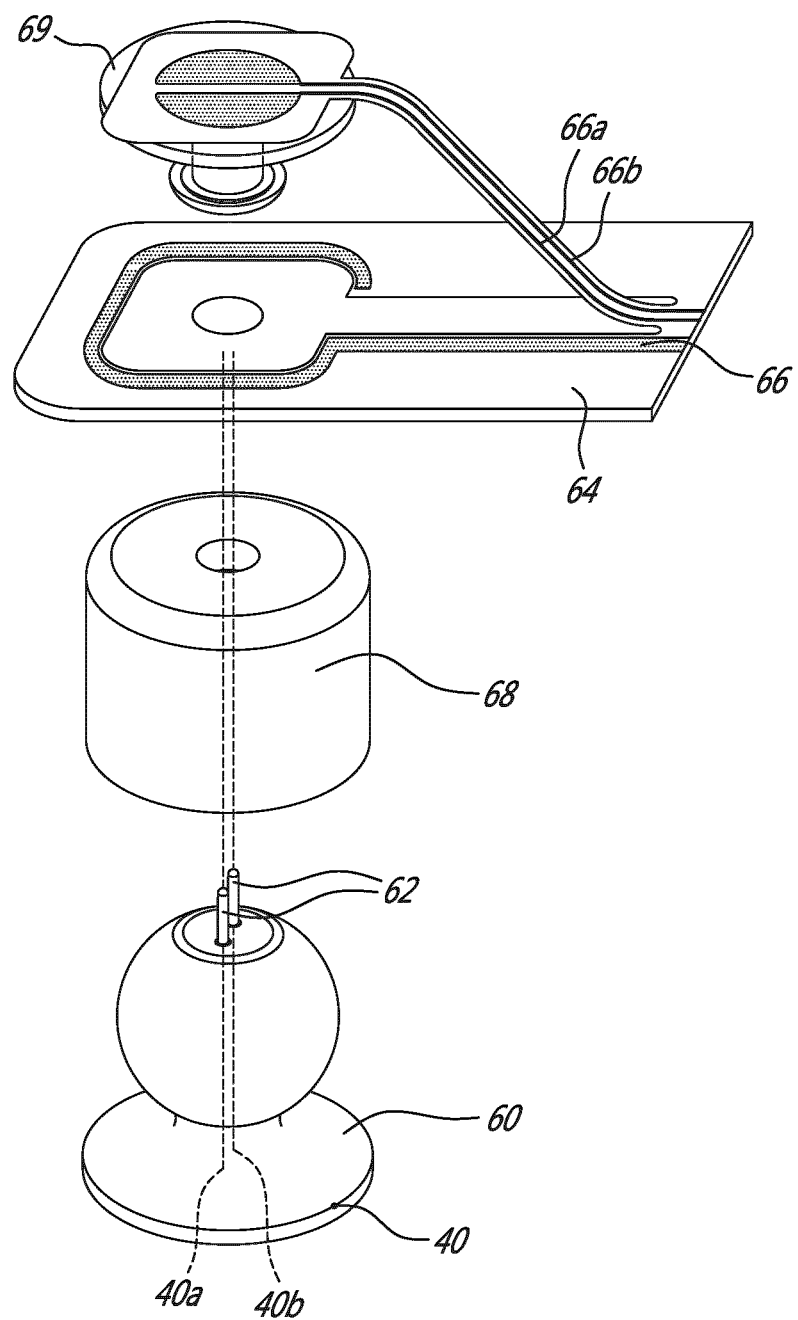
FIG. 6 is an exploded view showing a second example of a snap-button connector having more than one electrical connection therein.
Figure 7:
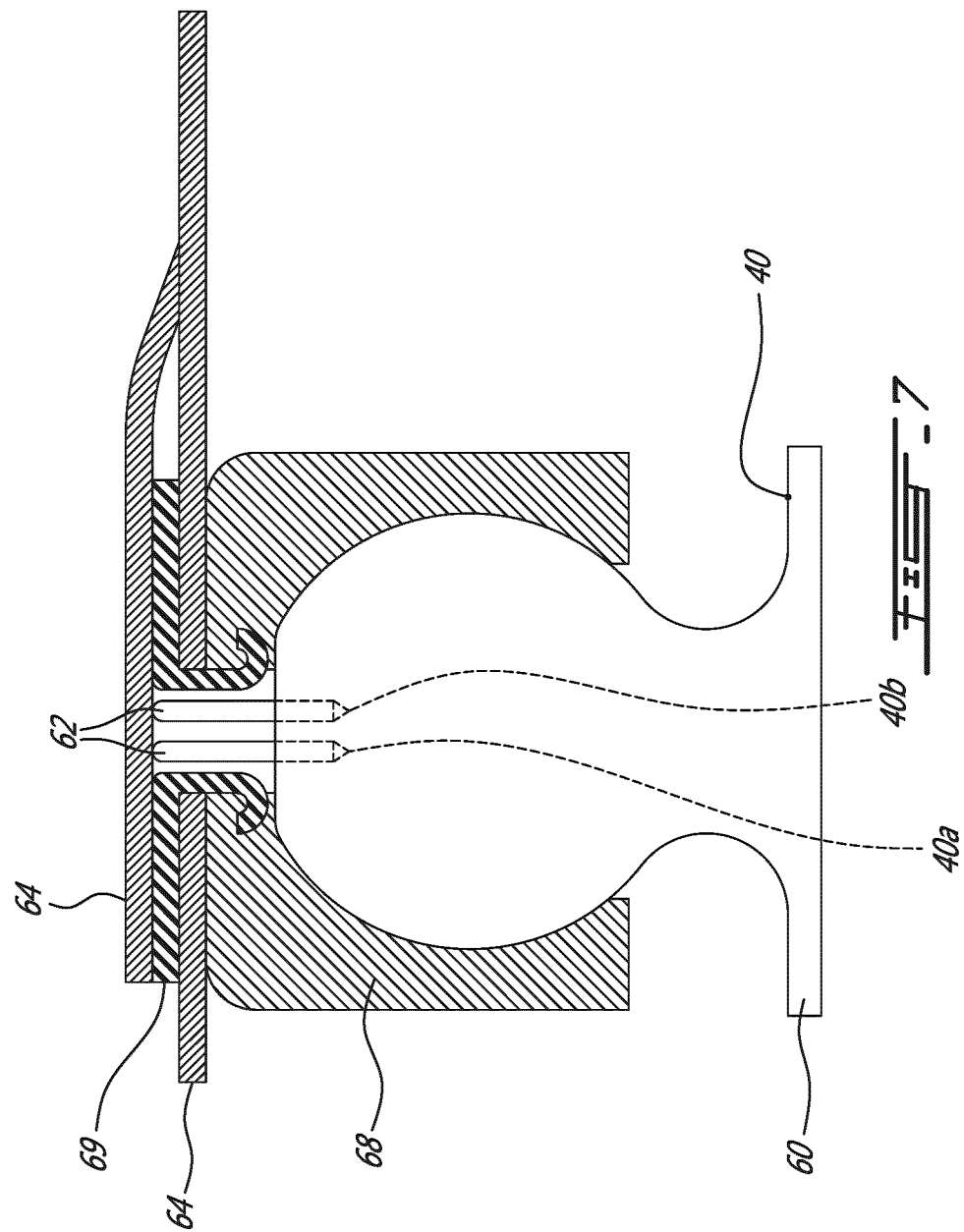
FIG. 7 is a cross-sectional view of the snap-button connector of FIG. 6.
Figure 8:
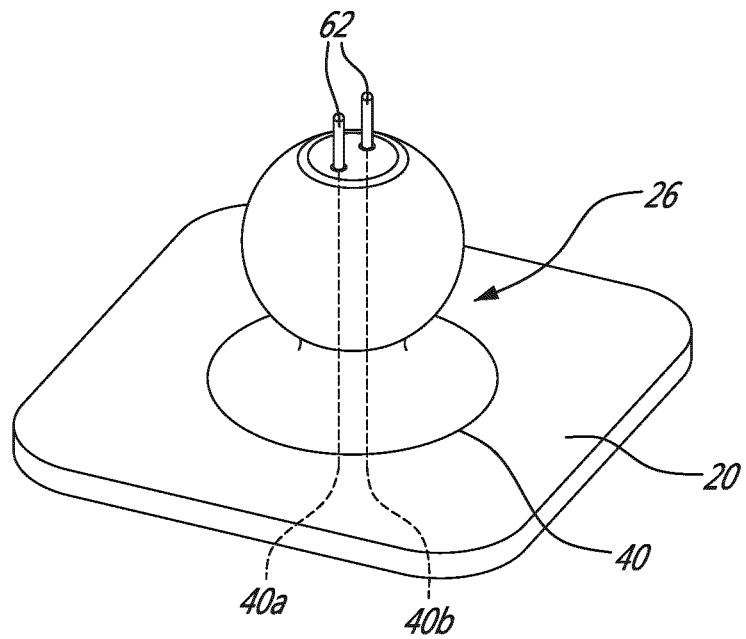
FIGS. 8 and 9 show how a snap button connector having three electrical connections can be used on an external multi-contact electrode.
Figure 9:
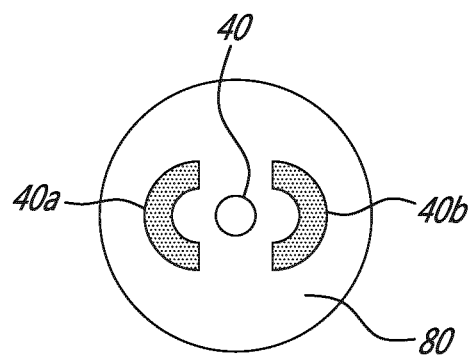

FIGS. 6 and 7 show an alternate embodiment to FIGS. 4 and 5, where the complementary PCB module 70 shown in FIGS. 4 and 5 is omitted. FIGS. 8 and 9 shows another embodiment of a multiple-signal connector configuration including a snap-button connector 26 made integral to the flexible bandage-like housing 20 and where three independent electrical contacts 40, 40a and 40c are integrated to an external multi-contact electrode 80.

Figure 10:
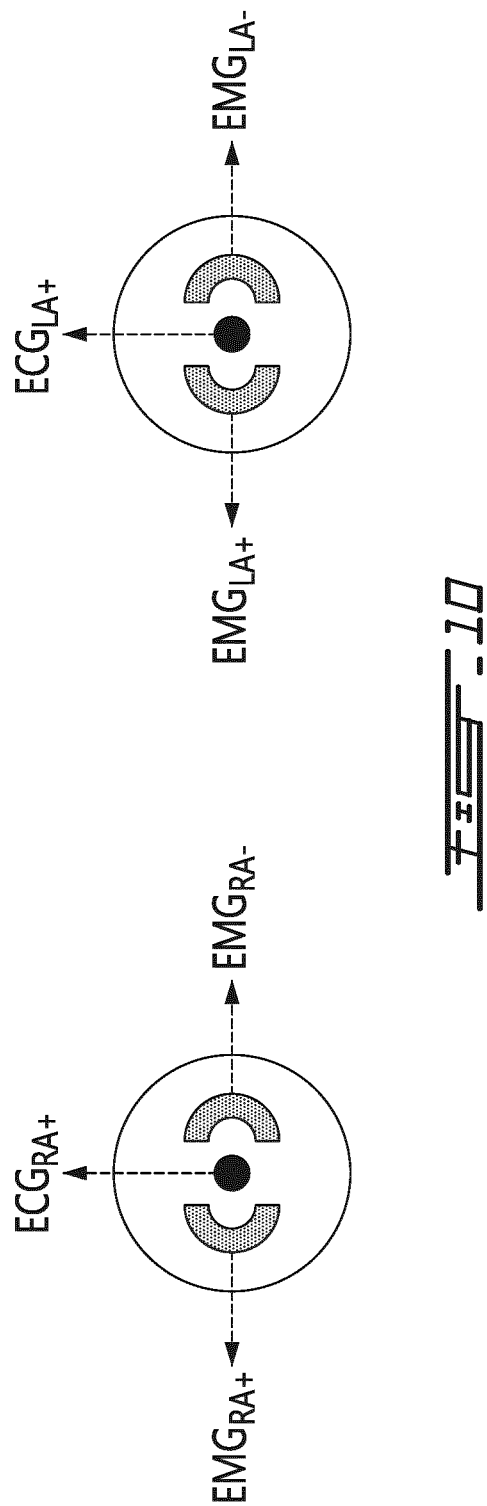
FIG. 10 shows an example of how two external multi-contact electrodes can be used in a Left-Arm-Right Arm configuration to reduce EMG noise from a one lead ECG signal.

As shown in FIG. 10, multi-signal connectors can be used for other reasons than increasing data transfer speed. For instance, in a case where multiple independent electrical contacts are provided, the multiple electrical paths can be used to obtain the differential measurement of the ECG signal along with two local measurements of EMG physiological noise, one per electrode (using three electrical paths per connector). Using equations (1) to (5) provided herebelow, two local EMG noise signals (one from each electrode connector) are measured and the differential between those two local signals is then deducted from the valid ECG signal.

$$ECG_{Raw} = ECG_{RA+} - ECG_{LA+} + EMG_{Artifact} + \text{Other Artifacts} \quad (1)$$

$$EMG_{Artifact} = EMG_{RA} - EMG_{LA} \quad (2)$$

$$EMG_{RA} = EMG_{RA+} - EMG_{RA-} \quad (3)$$

$$EMG_{LA} = EMG_{LA+} - EMG_{LA-} \quad (4)$$

$$ECG_{NoEMG} = ECG_{RA+} - ECG_{LA+} - (EMG_{RA} - EMG_{LA}) + \text{Other Artifacts} \quad (5)$$

This technique of using a plurality of input signals can be used to reduce the presence of undesired EMG noise or other physiological noises from a targeted ECG signal and thus provide a better signal quality. In another embodiment, the plurality of independent electrical paths per connector can be used for measurement of the local EMG signal (as the targeted signal of interest) in a view of managing size and complexity of EMG sensors. In such an embodiment, EMG sensors would have similar properties as found with ECG electrodes: one flexible single-use adhesive sensing electrode per targeted muscle with one snap button connector.

In an alternate embodiment, instead of having mechanical connectors having two or more independent electrical paths (electrical connections), a greater plurality of mechanical connectors having single electrical paths can be used for a similar electrical/electronic behaviour.

As can be understood, the examples described above and illustrated are intended to be exemplary only. The scope is indicated by the appended claims.

What is claimed is:

1. A method of using a physiological data acquirer housed in a flexible housing having a first snap-button connector and a second snap-button connector made integral to the housing and being adapted to matingly receive snap-button connectors of electrodes externally to the housing, the physiological data acquirer having an integrated battery, the method comprising:
    individually engaging the first and second snap-button connectors of the physiological data acquirer with the mating snap-button connectors of the electrodes;
    acquiring physiological data from a mammal with the physiological data acquirer, via the electrodes and via the engaged snap-button connectors, while the engaged snap-button connectors, and the electrodes in contact with a body of the mammal, hold the physiological data acquirer on the body of the mammal;
    disconnecting the first and second snap-button connectors of the physiological data acquirer from the mating snap-button connectors of the electrodes;
    connecting the first and second snap-button connectors of the physiological data acquirer to corresponding mating connectors of an external device; and
    extracting the acquired physiological data from the physiological data acquirer to the external device via the connected first and second snap-button connectors.

2. The method of claim 1 wherein the step of extracting data includes transferring data over at least two electrical paths across each snap-button connector of the physiological data acquirer.

3. The method of claim 1 wherein the step of acquiring includes transferring data over at least two electrical paths across each snap-button connector of the physiological data acquirer.

4. The method of claim 1 wherein the physiological data acquirer has two connectors.

5. The method of claim 1 wherein the first and second snap-button connectors are female snap-button connectors, and the electrodes are two off-the-shelf electrodes each having a mating male snap-button connectors.

6. The method of claim 1, wherein the physiological data acquirer has an electronic circuit encapsulated in the flexible housing, the electronic circuit having an analog switch being operable to selectively switch a connection from the first and second snap-button connectors to different components of the electronic circuit, to selectively switch between a data acquisition mode and a data extraction mode.

7. The method of claim 6, wherein the encapsulated electronic circuit has an analog front end, a micro-controller unit (MCU) and a memory operable in said data acquisition mode upon said analog switch connecting the analog front end to the snap-button connectors of the physiological data acquirer; the analog switch being further operable to connect the MCU to the first and second snap-button connectors of the physiological data acquirer for operating in said data extraction mode.

8. The method of claim 6, wherein the encapsulated electronic circuit has a data acquisition module powerable by the integrated battery, and a data extraction module, the analog switch being operable to selectively connect one of the data acquisition module and the data extraction module to the first and second snap-button connectors, thereby effecting said switch between said data acquisition mode and said data extraction mode.

9. The method of claim 6, wherein the physiological data acquirer further comprises a power activation system, wherein the analog switch is further configured to direct a signal to the power activation system during a sleep mode, the power activation system being configured to detect an activation signal when the electrodes have been connected to the first and second snap-button connectors of the physiological data acquirer and when the electrodes have been applied to the body of a user, and activate the data acquisition mode based on this signal.

10. The method of claim 9, wherein the power activation system is further configured to monitor an internal clock and automatically trigger de-activation of the data acquisition mode once a predetermined amount of time has elapsed.

11. The method of claim 6, wherein the physiological data acquirer further comprises a power management circuit, wherein the analog switch is further configured to shunt electrical power to the power management circuit upon operating in a battery charging mode, and the power management circuit is configured to manage charging of the battery, returning the analog switch to a detection mode upon detecting full charge of the battery.

12. The method of claim 6 wherein upon transition between data acquisition mode and data extraction mode, the analog switch is automatically reconfigured by the system to switch the connection between the first and second snap-button connectors and the different components of the electronic circuit.

13. A physiological data acquirer housed in a flexible housing having a first connector and a second connector made integral to the housing and being adapted to matingly receive corresponding electrodes externally to the housing, the physiological data acquirer having an integrated battery, and an electronic circuit encapsulated in the flexible housing, the electronic circuit having an analog switch being operable to selectively switch a connection from the first and second connectors to different components of the electronic circuit, to selectively switch between a data acquisition mode and a data extraction mode, wherein:

in the data acquisition mode, the physiological data acquirer is configured to acquire physiological data from a mammal via the electrodes and the first and second connectors, when the first and second connectors are engaged with snap-button connectors of the electrodes and the electrodes are in contact with a body of the mammal, and, in the data extraction mode, the physiological data acquirer is configured to allow the physiological data to be extracted by an external device, when the first and second connectors are engaged with snap-button connectors of the external device.

14. The physiological data acquirer of claim 13 wherein the encapsulated electronic circuit has an analog front end, a micro-controller unit (MCU) and a memory operable in said data acquisition mode upon said analog switch connecting the analog front end to the first and second connectors of the physiological data acquirer; the analog switch being further operable to connect the MCU to the first and second connectors of the physiological data acquirer for operating in said data extraction mode.

15. The physiological data acquirer of claim 13 wherein the encapsulated electronic circuit has a data acquisition module powerable by the integrated battery, and a data extraction module, the analog switch being operable to selectively connect one of the data acquisition module and the data extraction module to the first and second connectors, thereby effecting said switch between said data acquisition mode and said data extraction mode.

16. The physiological data acquirer of claim 13 further comprising a power activation system, wherein the analog switch is further configured to direct a signal to the power activation system during a sleep mode, the power activation system being configured to detect an activation signal when the electrodes have been connected to the first and second connectors of the physiological data acquirer and when the electrodes have been applied to the body of a user, and activate the data acquisition mode based on this signal.

17. The physiological data acquirer of claim 13 further comprising a power management circuit, wherein the analog switch is further configured to shunt electrical power to the power management circuit upon operating in a battery charging mode, and the power management circuit is configured to manage charging of the battery, returning the analog switch to a detection mode upon detecting full charge of the battery.

18. A method of using a physiological data acquirer housed in a flexible housing having at least two snap-button connectors made integral to the housing and being adapted to matingly receive snap-button connectors of electrodes externally to the housing, the physiological data acquirer having an integrated battery, the method comprising:

individually engaging the snap-button connectors of the physiological data acquirer with the mating snap-button connectors of the electrodes;

acquiring physiological data from a mammal with the physiological data acquirer, via the electrodes and via the engaged snap-button connectors, while the engaged snap-button connectors, and the electrodes in contact with a body of the mammal, hold the physiological data acquirer on the body of the mammal;

disconnecting the snap-button connectors of the physiological data acquirer from the mating snap-button connectors of the electrodes;

connecting the snap-button connectors of the physiological data acquirer to corresponding mating connectors of an external device; and extracting the acquired physiological data from the physiological data acquirer to the external device via the connected snap-button connectors;

wherein the physiological data acquirer has an electronic circuit encapsulated in the flexible housing, the electronic circuit having an analog switch being operable to selectively switch a connection from the snap-button connectors to different components of the electronic circuit, to selectively switch between a data acquisition mode and a data extraction mode, and wherein the physiological data acquirer further comprises a power activation system, wherein the analog switch is further configured to direct a signal to the power activation system during a sleep mode, the power activation system being configured to detect an activation signal when the electrodes have been connected to snap-button connectors of the physiological data acquirer and when the electrodes have been applied to the body of a user, and activate the data acquisition mode based on this signal.

19. A method of using a physiological data acquirer housed in a flexible housing having at least two snap-button connectors made integral to the housing and being adapted to matingly receive snap-button connectors of electrodes externally to the housing, the physiological data acquirer having an integrated battery, the method comprising:

individually engaging the snap-button connectors of the physiological data acquirer with the mating snap-button connectors of the electrodes;

acquiring physiological data from a mammal with the physiological data acquirer, via the electrodes and via the engaged snap-button connectors, while the engaged snap-button connectors, and the electrodes in contact with a body of the mammal, hold the physiological data acquirer on the body of the mammal;

disconnecting the snap-button connectors of the physiological data acquirer from the mating snap-button connectors of the electrodes;

connecting the snap-button connectors of the physiological data acquirer to corresponding mating connectors of an external device; and extracting the acquired physiological data from the physiological data acquirer to the external device via the connected snap-button connectors, wherein the physiological data acquirer has an electronic circuit encapsulated in the flexible housing, the electronic circuit having an analog switch being operable to selectively switch a connection from the snap-button connectors to different components of the electronic circuit, to selectively switch between a data acquisition mode and a data extraction mode, wherein the physiological data acquirer further comprises a power management circuit, and wherein the analog switch is further configured to shunt electrical power to the power management circuit upon operating in a battery charging mode, and the power management circuit is configured to manage charging of the battery, returning the analog switch to a detection mode upon detecting full charge of the battery.

20. A method of using a physiological data acquirer housed in a flexible housing having at least two snap-button connectors made integral to the housing and being adapted to matingly receive snap-button connectors of electrodes externally to the housing, the physiological data acquirer having an integrated battery, the method comprising:

individually engaging the snap-button connectors of the physiological data acquirer with the mating snap-button connectors of the electrodes;

acquiring physiological data from a mammal with the physiological data acquirer, via the electrodes and via the engaged snap-button connectors, while the engaged snap-button connectors, and the electrodes in contact with a body of the mammal, hold the physiological data acquirer on the body of the mammal;

disconnecting the snap-button connectors of the physiological data acquirer from the mating snap-button connectors of the electrodes;

connecting the snap-button connectors of the physiological data acquirer to corresponding mating connectors of an external device; and extracting the acquired physiological data from the physiological data acquirer to the external device via the connected snap-button connectors wherein the physiological data acquirer has an electronic circuit encapsulated in the flexible housing, the electronic circuit having an analog switch being operable to selectively switch a connection from the snap-button connectors to different components of the electronic circuit, to selectively switch between a data acquisition mode and a data extraction mode, and wherein upon transition between data acquisition mode and data extraction mode, the analog switch is automatically reconfigured by the system to switch the connection between the snap-button connectors and the different components of the electronic circuit.

21. The method of claim 18, wherein the power activation system is further configured to monitor an internal clock and automatically trigger de-activation of the data acquisition mode once a predetermined amount of time has elapsed.

22. A physiological data acquirer housed in a flexible housing having two connectors made integral to the housing and being adapted to matingly receive corresponding electrodes externally to the housing, the physiological data acquirer having an integrated battery, and an electronic circuit encapsulated in the flexible housing, the electronic circuit having an analog switch being operable to selectively switch a connection from the connectors to different components of the electronic circuit, to selectively switch between a data acquisition mode and a data extraction mode, further comprising a power activation system, wherein the analog switch is further configured to direct a signal to the power activation system during a sleep mode, the power activation system being configured to detect an activation signal when the electrodes have been connected to connectors of the physiological data acquirer and when the electrodes have been applied to the body of a user, and activate the data acquisition mode based on this signal.

23. A physiological data acquirer housed in a flexible housing having two connectors made integral to the housing and being adapted to matingly receive corresponding electrodes externally to the housing, the physiological data acquirer having an integrated battery, and an electronic circuit encapsulated in the flexible housing, the electronic circuit having an analog switch being operable to selectively switch a connection from the connectors to different components of the electronic circuit, to selectively switch between a data acquisition mode and a data extraction mode, further comprising a power management circuit, wherein the analog switch is further configured to shunt electrical power to the power management circuit upon operating in a battery charging mode, and the power management circuit is configured to manage charging of the battery, returning the analog switch to a detection mode upon detecting full charge of the battery.

* * * * *